United States Patent [19]

Ciullo

[11] Patent Number: 4,471,768

[45] Date of Patent: Sep. 18, 1984

[54] FRACTURE POSITIONER

[76] Inventor: Jerome V. Ciullo, 2831 Baltane, West Bloomfield, Mich. 48033

[21] Appl. No.: 432,069

[22] Filed: Sep. 30, 1982

[51] Int. Cl.³ .............................................. A61F 5/00
[52] U.S. Cl. .................................................... 128/83
[58] Field of Search .................. 128/69, 82, 83, 80 R; 30/120.1, 120.2, 120.3, 120.4, 120.5

[56] References Cited

U.S. PATENT DOCUMENTS 2,291,413  7/1942  Siebrandt .
2,758,622  8/1956  Greenblatt ......................... 30/120.4
2,985,168  5/1961  Jonas et al. .
3,759,251  9/1973  Adams ................................. 128/69

FOREIGN PATENT DOCUMENTS 41449  10/1916  Sweden ............................... 30/120.3
19608  of 1897  United Kingdom ................ 30/120.4
384772  12/1932  United Kingdom ................ 30/120.4

Primary Examiner—John D. Yasko
Attorney, Agent, or Firm—Harness, Dickey & Pierce

[57] ABSTRACT

This disclosure relates to a fracture positioning device having a pair of arms with ends pivotally attached and which may be used to provide positive forces necessary to position bone fracture fragments during surgery.

12 Claims, 2 Drawing Figures

FRACTURE POSITIONER

BACKGROUND AND SUMMARY OF THE INVENTION

This invention relates to medical instruments in general, and more particularly to a fracture positioning device especially well adapted for use in a sterile field during surgery.

When positioning fractured bones during surgery, the treating surgeon may require image intensification of X-ray assistance to best locate proper bone alignment or positioning. In addition, the application of substantial force may be necessary to obtain proper bone positioning. It would thus be desirable if a device could be provided which would facilitate the proper application of sufficient force to obtain desired bone positioning while allowing the surgeon to remain out of the field of radiation used for imaging.

Accordingly, the fracture positioner of the present invention provides an instrument that will permit substantial forces to be applied for positioning fracture fragments for intramedullary fixation of a bone with minimal damage to neurovascular structures and soft tissue from compressive forces. The instrument also permits a treating physician or surgeon to remain out of a field of radiation when said device is used in conjunction with image intensification or X-ray.

In addition, the bone fracture positioning device of this invention is simple in design, inexpensive to manufacture, rugged in construction, easy to use and efficient in operation. Still further advantages and features of the present invention will become apparent from a reading of the detailed description of the preferred embodiment and reference to the drawing.

DETAILED DESCRIPTION OF THE PREFERRED EMBODIMENT

Figure 1:
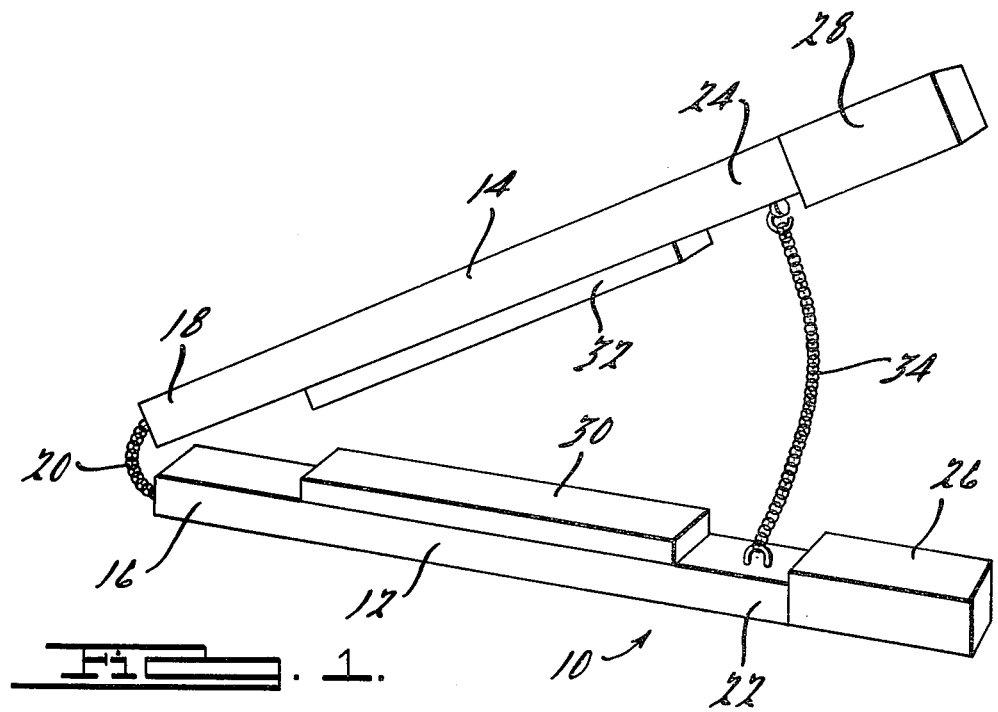
FIG. 1 is a perspective view of a preferred embodiment of the present invention, shown in an open position.

Referring now to the drawings, which set forth a preferred embodiment of the present invention, FIG. 1 shows a fracture positioner device 10 made in accordance with the present invention. Fracture positioner 10 comprises a pair of arms 12 and 14 having distal ends 16 and 18 pivotally attached by a chain 20 and having proximal ends 22 and 24 which carry hand grips 26 and 28 respectively. Intermediate distal end 16 and proximal end 22, arm 12 carries a resilient pad 30 while intermediate proximal end 18 and opposite end 24, arm 14 carries a resilient pad 32. A safety chain 34 is secured between opposite ends 22 and 24.

Figure 2:
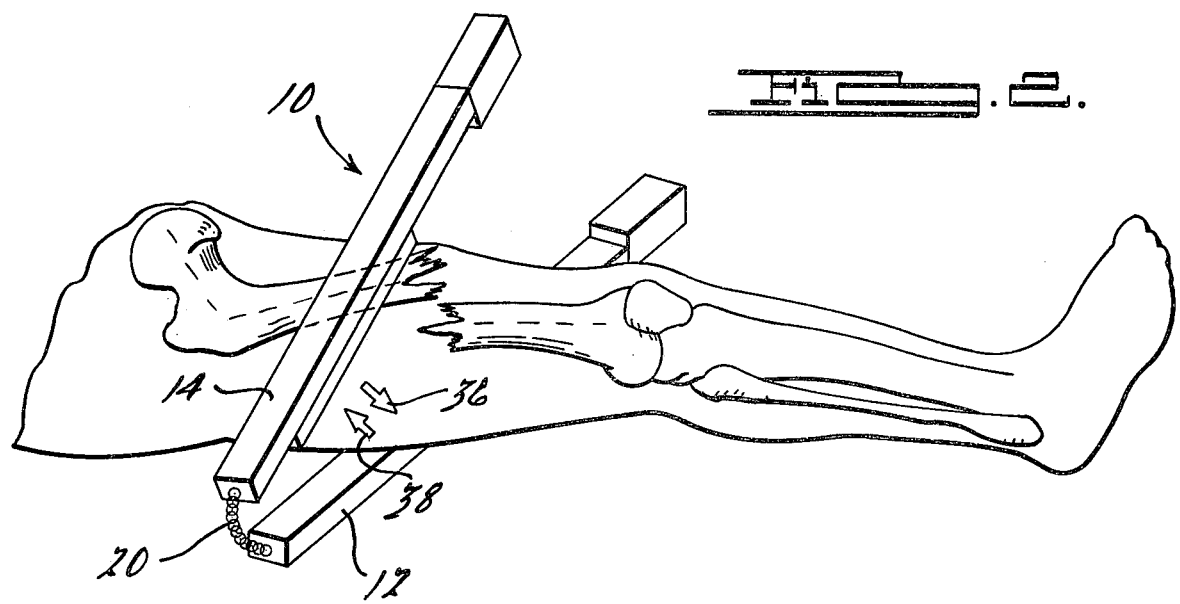
FIG. 2 is a perspective view of the present invention in operative association with a fractured leg.

Resilient pads 30 and 32 are preferably resilient pads made of relatively high resiliency material such as polyurethane foam and must, of course, be capable of withstanding sterilization procedures. Pads 30 and 32 can be secured to arms 12 and 14 respectively by any suitable means and are carried in facing relationship and generally medially on said arms 12 and 14 so as to be adapted to engage surfaces of a limb when positioned for use as illustrated in FIG. 2. Resilient pads 30 and 32 provide a measure of protection from injury to neurovascular structures and soft tissues of a limb during application of compressive forces required for intramedullary fixation of bone fracture fragments when fracture positioner 10 is used.

Chain 34 can be fixedly secured to one of opposite ends 22 and 24 of arms 12 and 14 by any suitable fastener and detachably secured to the other of ends 22 and 24 by any suitable fastener, such as a hook and loop type fastening system. Chain 34 is a safety element and provides means for preventing fracture positioner 10 from falling out of a sterile field when used during surgery should the surgeon release both grips 26 and 28. It will, of course, be appreciated that the safety element shown as chain 34 could alternatively be provided by another flexible length such as a cloth strap, rope or the like.

In use, with detachable end of safety chain 34 detached, the surgeon will manually grip hand grips 26 and 28 to manipulate positioner 10 with arms 12 and 14 placed on opposite sides of a limb and with resilient pads 30 and 32 placed so as to have facing surfaces engaging said limb. The detached end of safety chain 34 is then attached and the surgeon applies positive compressive force as illustrated by arrows 36 and 38 in FIG. 2. Through skilled manipulation of arms 12 and 14, the fracture fragments can be moved back into proper position for fixation and healing in accordance with known surgical procedures.

While the above description constitutes the preferred embodiment of the present invention, it will be appreciated that the invention is susceptible to modification, variation and change without departing from the proper scope or fair meaning of the accompanying claims.

I claim:

1. A fracture positioning device comprising a pair of arms each having a distal end and a proximal end; pivot means for pivotally attaching the distal ends of said arms, said pivot means permitting movement of said arms towards one another in a clamping direction and permitting substantial movement relative to one another in a direction transverse to said clamping direction for moving fracture fragments into proper position for fixation; a resilient pad carried generally medially on each of said arms; and a safety element detachably connecting the proximal end of each of said arms.

2. The device according to claim 1, wherein said pivot means for pivotally attaching the distal ends of said arms comprises a chain.

3. The device according to claim 1, wherein each said resilient pad is fixedly secured to said arms.

4. The device according to claim 1 wherein each said resilient pad is removably secured to said arms.

5. The device according to claim 1, wherein said safety element comprises a chain fixedly secured to one of said arms and detachably secured to the other of said arms.

6. The device according to claim 1 wherein the proximal end of each of said arms has a hand grip thereon.

7. The device according to claim 2 wherein each said resilient pad is fixedly secured to one of said arms.

8. The device of claim 2 wherein each said resilient pad is removably secured to one of said arms.

9. The device of claim 7 wherein said safety element comprises a chain fixedly secured to one of said arms and detachably secured to the other of said arms.

10. The device of claim 8 wherein said safety element comprises a chain fixedly secured to one of said arms and detachably secured to the other of said arms.

11. The device of claim 9 wherein the proximal end of each of said arms has a hand grip thereon.

12. The device of claim 10 wherein the proximal end of each of said arms has a hand grip thereon.

* * * * *